United States Patent [19]

Anderson

[11] 3,953,525

[45] Apr. 27, 1976

[54] α-SUBSTITUTED-4-(2,2-DIMETHYL-1-HYDROXYPROPYL)BENZYL ALCOHOLS AND ESTERS

[75] Inventor: Paul L. Anderson, Dover, N.J.

[73] Assignee: Sandoz, Inc., E. Hanover, N.J.

[22] Filed: Nov. 19, 1974

[21] Appl. No.: 525,177

[52] U.S. Cl............................ 260/618 R; 260/483; 424/343; 424/298
[51] Int. Cl.$^2$....................................... C07C 31/18
[58] Field of Search .................. 260/618 R

[56] References Cited
UNITED STATES PATENTS 2,733,281   1/1956   Dreisbach et al. .............. 260/618 R
2,967,854   1/1961   Bungs............................... 260/618 R

OTHER PUBLICATIONS

Johnson et al., Bioorg. Chem. 1973, 2(2), pp. 99–110.

*Primary Examiner*—James O. Thomas, Jr.
*Assistant Examiner*—James H. Reamer
*Attorney, Agent, or Firm*—Gerald D. Sharkin; Robert S. Honor; Thomas O. McGovern

[57] ABSTRACT

α-substituted-4-(2,2-dimethyl-1-hydroxypropyl) benzyl alcohols and esters, e.g., α-methyl-4-(2,2-dimethyl-1-hydroxypropyl) benzyl alcohol, are prepared from the corresponding 1-(4-alkanoylphenyl) alkanols and derivatives and are useful as hypolipidemic agents.

3 Claims, No Drawings

α-SUBSTITUTED-4-(2,2-DIMETHYL-1-HYDROXY-PROPYL)BENZYL ALCOHOLS AND ESTERS

This invention relates to α-substituted-4-(2,2-dimethyl-1-hydroxypropyl) benzyl alcohols and esters, their method of preparation and their use in pharmaceutical compositions.

The compounds of this invention may be represented by the following structural formula:

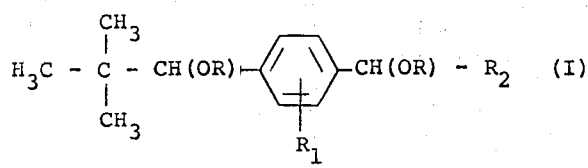

where
R is hydrogen or lower alkanoyl having 1 to 4 carbon atoms, e.g., acetyl, propionyl, and the like;
$R_1$ is hydrogen or halo having an atomic weight of about 19 to 80, i.e., fluoro, chloro, or bromo; and
$R_2$ is lower alkyl, i.e., alkyl having 1 to 4 carbon atoms, e.g., methyl, ethyl, isopropyl and the like, provided that both substituents R are the same.

The compounds of formula (I) in which R represents hydrogen may be prepared according to the following reaction scheme:

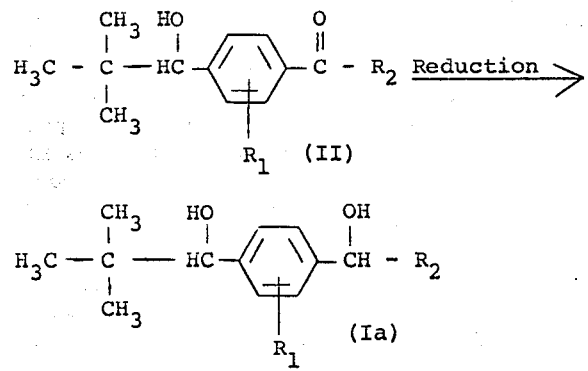

where $R_1$ and $R_2$ are as defined above.

The compounds of formula (Ia) are prepared by reducing a compound of formula (II) with an alkali metal hydride, such as potassium aluminum hydride or lithium aluminum hydride, an organo aluminum hydride, e.g., diisobutyl aluminum hydride, triisobutyl aluminum hydride and the like or sodium aluminum diethyl dihydride, the latter being especially preferred, in the presence of an inert organic solvent. Although the particular solvent used is not critical, it is preferred that the reaction be carried out in the presence of an aromatic hydrocarbon, such as benzene, toluene and the like, or an ether, such as tetrahydrofuran, diethylether and the like, preferably toluene. The temperature at which the reaction is carried out is not critical, but it is preferred that the reaction be carried out between 0° to 30°C., preferably from about 20° to 25°C. The reaction may be run from about 30 minutes to 24 hours, preferably from about 30 minutes to 4 hours. The product is recovered using conventional techniques, e.g., recrystallization.

The compounds of formula (I) in which R represents lower alkanoyl may be prepared according to the following reaction scheme:

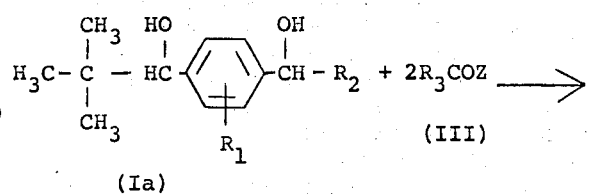

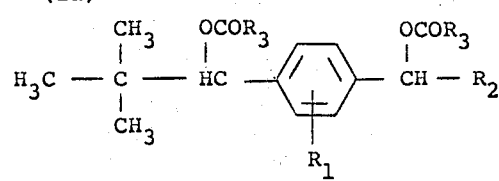

where
Z is halo having an atomic weight of about 35 to 80, or $R_3OCO-$;
$R_3$ is lower alkyl having 1 to 3 carbon atoms and
$R_1$ and $R_2$ are as defined above.

The compounds of formula (Ib) are prepared by treating a compound of the formula (Ia) with a compound of the formula (III) in an inert solvent. Although the particular solvent used is not critical, it is preferred that the reaction be carried out in an inert solvent such as tetrahydrofuran or ethyl ether, aromatic hydrocarbons such as benzene, toluene and xylene, halogenated hydrocarbons such as methylene dichloride or chloroform, especially pyridine when Z is $R_3OCO-$. The temperature at which the reaction is carried out is not critical, but it is preferred that the reaction be carried out between about 10° to 150°C., preferably between 20° to 50°C., especially 20° to 30°C. The time of the reaction also is not critical, but it is preferred that the reaction be run for 6 to 48 hours, especially 20 to 28 hours. When Z is halo, it is preferred that an acid binding agent such as sodium or potassium carbonate, pyridine, triethylamine and the like be added to the reactants. The compounds of formula (Ib) are recovered using conventional techniques, e.g., titration.

The compounds of formula (II) are prepared by the following reaction scheme:

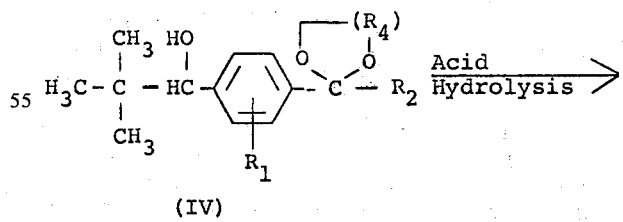

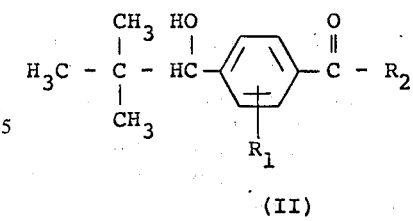

where $R_4$ is $-(CH_2)-$, $-CH_2CH_2-$ or $-C(CH_3)_2C-H_2-$, and $R_1$ and $R_2$ are as defined above.

The compounds of formula (II) are prepared by treating a compound of the formula (IV) with an aqueous inorganic acid. The acid used in the reaction can be any mineral acid, such as sulfuric acid, hydrochloric acid and the like, preferably in dilute form. Although a solvent is not required, it is preferred that the reaction be carried out in a water-miscible solvent such as organic acids, e.g., acetic acid, ethanol dioxane, tetrahydrofuran, and the like, especially acetic acid. The temperature at which the reaction is carried out is not critical, but it is preferred that the reaction be run between 0° to 100°C., preferably between about 80° to 100°C. The time of the reaction also is not critical, but it is preferred that the reaction be run for 1 to 24 hours, especially 1 to 4 hours. The compound of formula (II) is recovered using conventional techniques, e.g., chromatography.

The compounds of formula (IV) are prepared by the following reaction scheme:

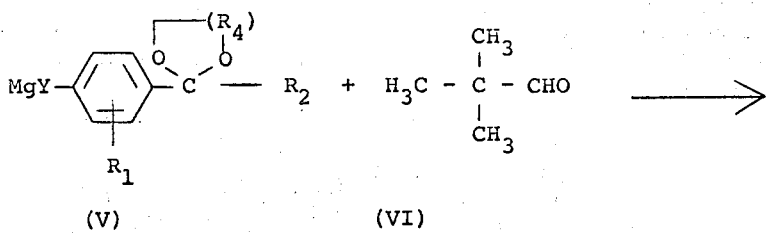

where
Y is halo having an atomic weight of from about 35 to 80, and
$R_1$, $R_2$ and $R_4$ are as defined above.

The compounds of formula (IV) are prepared by reacting a Grignard reagent of the formula (V) with a compound of the formula (VI) in an inert solvent. It is preferred that the reaction be carried out in an inert solvent such as ethers, e.g., diethyl ether, tetrahydrofuran and the like or aromatic hydrocarbons, e.g., benzene, toluene, xylene and the like, especially tetrahydrofuran. The temperature at which the reaction is carried out is not critical, but it is preferred that the reaction be carried out between about 20° to 200°C., preferably between about 30° to 150°C., especially at the reflux temperature of the reaction medium. The time of the reaction also is not critical, but it is preferred that the reaction be run for 1 hour to 24 hours, especially 2 hours to 16 hours. It is also preferred that the reaction be carried out in an inert atmosphere such as argon, helium, or nitrogen, preferably nitrogen. The compounds of formula (IV) are recovered by conventional techniques, e.g., evaporation and recrystallization.

Many of the compounds of formulae (III), (V), and (VI) are known and may be prepared by methods described in the literature. Those compounds of formulae (III), (V) and (VI) not specifically disclosed may be prepared by analagous methods from known starting materials.

The compounds of formula (I) are useful because they possess pharmacological activity in animals. In particular, the compounds of formula (I) are useful as hypolipidemic agents in the treatment of lipidemia, in particular, hyperliproteinemia as indicated by the fall in cholesterol and triglyceride levels in male albino Wistar rats weighing 110–130 g. initially. The rats are maintain on drug-free laboratory chow diet for 7 days and then divided into groups of 6 to 10 animals. Each group, with the exception of the control, is then given orally 30 to 250 milligrams per kilogram of body weight per diem of the test compound for 6 days. At the end of this period, the animals are anesthetized with sodium hexobarbital and bled from the carotid arteries. Serum or plasma samples are collected and 1.0 ml. of the serum is added to 9.0 ml. redistilled isopropanol. Two autoanalyzer cupsful of a mixture of zeolite-copper hydroxide and Lloydds reagent (Kessler, G., and Lederer, H., 1965, Technicon Symposium, Mediad Inc., New York, 345–347) are added and the mixture is shaken for 1 hour. Cholesterol and triglyceride levels are determined simultaneously on the same sample by Technicon N 24A (cholesterol) and N-78 (triglyceride) methodology. The mean total serum cholesterol levels are then computed and the hypocholesterol activity is expressed as the fall in cholesterol levels as a percentage of the control level. The change in serum triglyceride levels induced by the drug is computed as a percentage of the control triglyceride levels.

For such use, the compounds of formula (I) may be administered orally or parenterally as such or admixed with conventional pharmaceutical carriers. They may be administered orally in such forms as tablets, dispersible powders, granules, capsules, syrups and elixirs, and parenterally as solutions, e.g., a sterile injectable aqueous solution. The compositions for oral use may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastrointestinal tract and thereby provide a sustained action over a longer period. Similarly, suspensions, syrups and elixirs may contain the active ingredient in admixture with any of the conventional excipients utilized in the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl-p-hydroxybenzoate. Capsules may contain the active ingredient alone or admixed with an inert solid diluent, e.g., calcium carbonate, calcium phosphate and kaolin. The injectable compositions are formulated as known in the art. These pharmaceutical preparations may contain up to about 90% of the active ingredient in combination with the carrier or adjuvant.

The hypolipidemic effective dosage of active ingredient employed for the treatment of lipidemia, in particular, hyperlipoproteinemia may vary depending on the particular compound employed, the mold of administration and the severity of the condition being treated. However, in general, satisfactory results are obtained for the hypolipidemic effect when the compounds of formula (I) are administered at a daily dosage of from about 4 milligrams to about 200 milligrams per kilogram of animal body weight, p.o., preferably given in divided doses two to four times a day, or in sustained release form. For most large mammals, the total daily dosage for both indications is from about 300 to about 3000 milligrams. Dosage forms suitable for internal use comprise from about 75 to 1500 milligrams of the active compound in intimate admixture with a solid or liquid pharmaceutically acceptable carrier or diluent.

A representative formuation suitable for oral administration is a tablet or capsule prepared by standard tableting or encapsulating techniques which contains the following and may be administered 2 to 4 times a day in the treatment of lipidemia:

| Ingredient | Weight (mg.) | |
|---|---|---|
| | tablet | capsule |
| α-methyl-4-(2,2-dimethyl-1-hydroxypropyl) benzyl alcohol | 100 | 100 |
| tragacanth | 10 | — |
| lactose | 247.5 | 300 |
| corn starch | 25 | |
| talcum | 15 | |
| magnesium stearate | 2.5 | |
| TOTAL | 400 mg. | 400 mg. |

EXAMPLE 1

1-(p-acetophenyl)-2,2-dimethylpropanol

STEP A: 1) 2-methyl-2-(4-[1-hydroxy-2,2-dimethylpropyl]- phenyl)-1,3-dioxolane.

In 1200 milliliters of toluene in a flask equipped with a Dean-Stark tube are dissolved 100 grams of p-bromoacetophenone; and to this solution is added 140 grams of ethylene glycol and 5 grams of p-toluenesulphonic acid. This mixture is refluxed until no further water collects in the Dean-Stark tube. After distilling off 600 milliliters of toluene, the remaining solution is decanted off and evaporated to dryness in vacuo to obtain 2-methyl-2-(p-bromophenyl)-1,3-dioxolane.

In 250 milliliters of tetrahydrofuran, 118 grams of the above dioxolane is dissolved. One quarter of this solution is then added to 12 grams of magnesium previously washed with chloroform, and refluxed with tetrahydrofuran for 20 minutes; and this mixture is refluxed 4 hours to initiate reaction. Additional dioxolane solution is thereafter added to maintain the refluxing without further heating. After the addition has been completed, 35 grams of 2,2-dimethylpropanal is added and the mixture is refluxed for 2 hours. The reactants are allowed to stand overnight and then poured onto ice-cold ammonium chloride solution. Tetrahydrofuran is added and the two layers formed are allowed to separate. The solvent layer is decanted off and the aqueous layer is extracted twice with 100 milliliters of tetrahydrofuran which are decanted off and combined with the remaining solvent layer. The organic phase is dried over anhydrous magnesium sulphate, filtered and evaporated to dryness to yield a yellow oil which is distilled at 120° to 150°C. at 30M and recrystallized from pentane/ether to yield 2-methyl- 2-(4-[1-hydroxy-2,2-dimethylpropyl]-phenyl)-1,3-dioxolane (m.p. 75°–80°C.).

When the above procedure is carried out using in place of the p-bromoacetophenone of Step A, an equivalent amount of 4-bromo-2-chloro-acetophenone or p-bromopropiophenone, there is obtained 2-methyl-2-(2-chloro-4-[1-hydroxy-2,2-dimethylpropyl]phenyl)-1,3-dioxolane or 2-ethyl-2-(4-[1-hydroxy-2,2-dimethylpropyl]-phenyl)-1,3-dioxolane.

STEP B: 1-(p-acetophenyl)-2,2-dimethylpropanol.

The above 2-methyl-2-(4-[1-hydroxy-2,2-dimethylpropyl]phenyl)-1,3-dioxolane is dissolved in 200 milliliters acetic acid and 65 milliliters of 6N hydrochloric acid are added. The solution is heated on a water bath at about 80°–110°C. for 2 hours and the acetic acid is then removed in vacuo. The residual oil is dissolved in chloroform and washed twice with water after which the chloroform layer is dried over anhydrous magnesium sulphate. The drying agent is filtered off. The chloroform is evaporated off from the filtrate and the oil obtained is recrystallized from pentane ether to obtain 1-(p-acetophenyl)- 2,2-dimethylpropanol (m.p. 66°–69°C.).

When the above reaction is carried out using in place of 2-methyl-2-(4-[1-hydroxy-2,2-dimethylpropyl]-phenyl)1,3-dioxolane, and equivalent amount of 2-methyl-2-(2-chloro-4-[1-hydroxy-2,2-dimethylpropyl]-phenyl)-1,3-dioxolane, or 2-ethyl-2-(4-[1-hydroxy-2,2-dimethylpropyl]-phenyl)-1,3-dioxolane, there is obtained 1-(2-chloro-p-acetophenyl)-2,2-dimethylpropanol or 1-(p-propionylphenyl)-2,2-dimethylpropanol.

EXAMPLE 2

α-methyl-4-(2,2-dimethyl-1-hydroxypropyl)benzyl alcohol

A mixture of 2.0 grams of 1-(p-acetophenyl)-2,2-dimethylpropanol dissolved in 150 ml. of dry tetrahydrofuran is prepared. To this solution is added 20 ml. of a 25% by weight solution of sodium aluminum diethyl dihydride in toluene. After the addition is completed, the mixture is stirred at room temperature for 30 minutes. The mixture is then cautiously poured onto 50 cc. of crushed ice. Anhydrous magnesium sulfate is added to take up the water, after which the drying agent is filtered off. The solvent is removed from the filtrate on a rotary evaporator leaving a solid residue which is recrystallized from methylene chloride to yield α-methyl-4-(2,2-dimethyl-1-hydroxypropyl)benzyl alcohol, m.p. 118°–121°C.

When the above reaction is carried out using in place of 1-(p-acetophenyl)-2,2-dimethylpropanol an equivalent amount of 1-(2-chloro-p-acetophenyl)-2,2-dimethylpropanol or 1-(p-propionylphenyl)-2,2-dimethylpropanol, there is obtained α-methyl-2-chloro-4-(2,2-dimethyl-1-hydroxypropyl)benzyl alcohol or α-ethyl-4-(2,2-dimethyl-1-hydroxypropyl)benzyl alcohol.

The compound of this example is useful as a hypolipidemic agent in mammals when administered at a dose of 100 milligrams 2 to 4 times a day.

EXAMPLE 3

1-[4-(1-acetoxy-2,2-dimethylpropyl)phenyl]-1-acetoxy propane

A mixture of 2.2 grams of α-ethyl-4-(2,2-dimethyl-1- hydroxypropyl)benzyl alcohol in 150 ml. dry pyridine is prepared. To this solution, 15 ml. of acetic anhydride is added at room temperature. The reaction mixture is allowed to stand overnight at room temperature; the following day, the pyridine and excess acetic anhydride are removed under reduced pressure on a rotary evaporator. The residual oil is dissolved in ether and washed with 2N hydrochloric acid, water, 2N sodium hydroxide, and finally with brine. The ether layer is dried over anhydrous magnesium sulfate, after which the drying agent is filtered off. The solvent is removed from the filtrate under reduced pressure on a rotary evaporator to give a clear water white oil which partially solidifies on cooling. The solid material is filtered off and washed with cold pentane and then dried to give 1-[4-(1-acetoxy-2,2-dimethylpropyl)phenyl]-1-acetoxy propane, m.p. 64°–65°C.

When the above reaction is carried out using in place of α-ethyl-4-(2,2-dimethyl-1-hydroxypropyl)benzyl alcohol an equivalent amount of α-methyl-2-chloro-4-(2,2-dimethyl-1-hydroxypropyl)benzyl alcohol or α-methyl-4-(2,2-dimethyl-1-hydroxypropyl)benzyl alcohol, there is obtained 1-[2-chloro-4-(1-acetoxy-2,2-dimethylpropyl)phenyl]-1-acetoxyethane or 1-[4-(1-acetoxy-2,2-dimethylpropyl)phenyl]-1-acetoxy ethane.

What is claimed is:

1. A compound of the formula

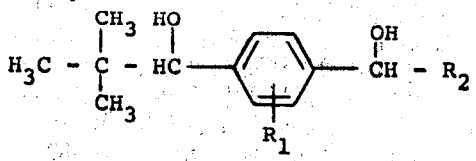

where $R_1$ is hydrogen or halo having an atomic weight of 19 80, and $R_2$ is lower alkyl.

2. A compound of the formula

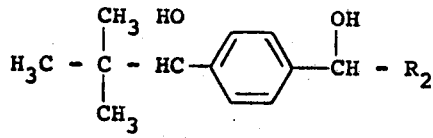

where $R_2$ is an defined in claim 1.

3. The compound of claim 2 which is α-methyl-4 (2,2-dimethyl-1-hydroxypropyl)benzyl alcohol.

* * * * *